(12) United States Patent
Modrovich

(10) Patent No.: US 7,595,170 B2
(45) Date of Patent: Sep. 29, 2009

(54) APPARATUS AND METHOD FOR MEASURING CONCENTRATIONS OF MOLECULES THROUGH A BARRIER

(76) Inventor: Ivan E. Modrovich, 1567 Spinnaker Dr., Suite 204, Ventura, CA (US) 93001

( * ) Notice: Subject to any disclaimer, the term of this patent is extended or adjusted under 35 U.S.C. 154(b) by 0 days.

(21) Appl. No.: 11/190,834

(22) Filed: Jul. 28, 2005

(65) Prior Publication Data
US 2006/0030031 A1    Feb. 9, 2006

Related U.S. Application Data

(60) Provisional application No. 60/598,896, filed on Aug. 5, 2004.

(51) Int. Cl.
C12Q 1/00    (2006.01)
C12Q 1/54    (2006.01)
G01N 27/00   (2006.01)
G01N 27/30   (2006.01)
G01N 33/53   (2006.01)

(52) U.S. Cl. .............. 435/14; 435/4; 435/5; 435/6; 435/7.1; 435/7.2; 435/7.32; 436/149; 422/50; 422/57; 422/82.01; 422/82.02

(58) Field of Classification Search .............. 435/4–7.2, 435/7.32
See application file for complete search history.

(56) References Cited

U.S. PATENT DOCUMENTS

| 2,482,773 | A | | 9/1949 | Hieronymus | |
|---|---|---|---|---|---|
| 3,823,706 | A | | 7/1974 | Davis | |
| 4,317,879 | A | * | 3/1982 | Busby et al. | 204/403.11 |
| 4,713,347 | A | * | 12/1987 | Mitchell et al. | 436/501 |
| 4,882,423 | A | * | 11/1989 | Taguchi et al. | 530/380 |
| 5,157,019 | A | * | 10/1992 | Glover et al. | 514/12 |
| 5,212,050 | A | * | 5/1993 | Mier et al. | 430/320 |
| 5,672,471 | A | * | 9/1997 | Durda et al. | 435/5 |
| 5,705,399 | A | * | 1/1998 | Larue | 436/501 |
| 6,022,948 | A | * | 2/2000 | Goldberg | 530/326 |
| 6,043,024 | A | | 3/2000 | Fesik et al. | |
| 6,096,509 | A | | 8/2000 | Okun et al. | |

(Continued)

FOREIGN PATENT DOCUMENTS

JP    410071268 A    3/1998

OTHER PUBLICATIONS

Biswas et al., "The molecular basis for pyrimidine-selective DNA binding: Analysis of calicheamicin oligosaccharide derivatives by capillary electrophoresis", 2000, J. Am. Chem. Soc., vol. 122, pp. 8413-8420.*

(Continued)

*Primary Examiner*—Unsu Jung
(74) *Attorney, Agent, or Firm*—Bacon & Thomas, PLLC

(57) ABSTRACT

An apparatus and method for detecting the presence and measuring the concentrations of molecules through a barrier and/or at a distance utilizes the principle of chemical/electrostatic attraction (hereinafter "affinity"), i.e., the affinity between charged atoms and molecules that cause their chemical interactions and reactions, to infer, based on the behavior of molecules on one side of the barrier, the presence and concentration of corresponding molecules on the other side of the barrier. The invention is useful, by way of example and not limitation, in non-invasively measuring glucose levels of diabetic patients.

9 Claims, 1 Drawing Sheet

U.S. PATENT DOCUMENTS

| | | |
|---|---|---|
| 6,100,045 A | 8/2000 | Van Es |
| 6,110,660 A | 8/2000 | Kriz et al. |
| 6,120,460 A * | 9/2000 | Abreu ................. 600/558 |
| 6,312,393 B1 | 11/2001 | Abreu |
| 6,321,588 B1 | 11/2001 | Bowers et al. |
| 6,322,963 B1 | 11/2001 | Bauer |
| 6,413,786 B1 | 7/2002 | Hansen et al. |
| 6,432,630 B1 | 8/2002 | Blankenstein |
| 6,656,430 B2 | 12/2003 | Sheppard, Jr. et al. |
| 6,699,724 B1 * | 3/2004 | West et al. ................. 436/525 |
| 6,784,854 B1 | 8/2004 | Yukl |
| 2003/0129618 A1 | 7/2003 | Moronne et al. |
| 2003/0148529 A1 | 8/2003 | Lewis et al. |
| 2003/0159523 A1 | 8/2003 | Renfro |
| 2003/0224530 A1 | 12/2003 | Anvar et al. |
| 2005/0221271 A1 * | 10/2005 | Murphy et al. ................. 435/4 |

OTHER PUBLICATIONS

Carbeck et al., "Protein charge ladders, capillary electrophoresis, and the role of electrostatics in biomolecular recognition", 1998, Acc. Chem. Res., vol. 31, pp. 343-350.*

Honig et al., "Classical electrostatics in biology and chemistry", 1995, Science, vol. 268, pp. 1144-1149.*

Moll et al., "Magnesium is required for specific DNA binding of the CREB B-ZIP domain", 2002, Nucleic Acids Res., vol. 30, pp. 1240-1246.*

Florin et al., "Adhesion forces between individual ligand-receptor pairs," Science, 1994, vol. 264, pp. 415-417.*

Barrett, "Homeopathy: The Ultimate Fake," [www] quackwatch.org/01Quackery Related Topics/homeo.htm (Dec. 28, 2003).

HiEnergy Technologies, Inc., "SuperSenzor," [www] hienergyic.com/products/supersenzor.htm (2003).

* cited by examiner

Measuring Molecule (MM)  Target Molecule (TM)  Attached Measuring – Target Complex (MM-TM Complex)

APPARATUS AND METHOD FOR MEASURING CONCENTRATIONS OF MOLECULES THROUGH A BARRIER

This application claims the benefit of provisional application No. 60/598,896, filed Aug. 5, 2004.

BACKGROUND OF THE INVENTION

1. Field of the Invention

This invention relates to an apparatus and method for detecting the presence of specified molecules, and in particular to an apparatus and method for detecting the presence and/or concentrations of molecules through a barrier. The invention infers the presence or concentration of the target molecules on one side of the barrier based on an analysis of measuring molecules that have an affinity for, i.e., are attracted to or repulsed by the target molecules, and that are situated on the other side of the barrier.

Although the description of the invention refers to "molecules," the invention is not limited to detection of molecules per se, but is broadly applicable to detection of the presence and/or concentration of constituents of molecules, including individual atoms, as well as to detection of chemical entities, both organic and inorganic, made up of molecules or groups of molecules. Furthermore, the measuring agents used to detect the presence of target entities may include constituents of molecules, including individual atoms, as well as chemical entities, both organic and inorganic, made up of molecules or groups of molecules. Therefore, while detection of molecules represents a specific embodiment of the invention, the invention in its broadest form relates to the detection and/or manipulation of target entities including chemicals, atoms, and molecules in general through a barrier, by means of complementary measuring agents also including chemicals, atoms, and molecules in general.

In one example, the invention enables blood glucose levels to be non-invasively measured by an external probe, based on changes in the orientation of glucose oxidase molecules suspended in a gel or some other gel-like viscous matrix as the probe is placed near the patient's skin. The orientation may be determined by measuring changes in an electrical property, such as resistivity, of the gel, or by detecting any other orientation-affected property of the gel or constituents of the gel, including magnetic or optical properties. The presence of target molecules may also be inferred by detecting properties of the gel that are affected by affinity-responsive properties of the molecules other than "orientation," such as changes in migration of measuring molecules through the gel in response to an applied field.

As another example, the invention may be used to detect the presence of c-reactive protein (CRP) specific antibodies based on the orientation of CRP specific monoclonal antibodies suspended in the gel.

2. Description of Related Art

Many physiological conditions can at present only be detected by drawing blood or other fluids from a patent for in vitro analysis. Drawing blood requires a skilled practitioner, and is painful, inconvenient, costly, and poses the risk of infection. As a result, many pathologies go undetected until they are relatively advanced, while others are extremely burdensome to monitor.

An example of a disease that requires frequent withdrawal of blood for testing is diabetes. Many attempts have been made to develop a painless, non-invasive, external device to monitor glucose levels. Various approaches have included electrochemical and spectroscopic technologies, such as near-infrared spectroscopy and Raman spectroscopy. Despite extensive efforts, however, none of these methods have yielded a non-invasive device or method for the in vivo measurement of glucose that is sufficiently accurate, reliable, convenient and cost-effective for routine use.

The present invention takes a different approach to in vivo measurement of blood or tissue constituents such as glucose. Instead, of attempting to directly measure constituent concentrations, the invention utilizes the molecular or atomic forces that cause chemical interactions and reactions, referred to herein as "affinity," to infer, based on the behavior of atoms or molecules on one side of a barrier, the presence and concentration of complementary atoms and molecules on the other side of the barrier. Such affinity forces have been studied recently with atomic force microscopy and were found capable of breaking strong chemical bonds. See, e.g., Grandbois et al., "*Affinity Imaging of Red Blood Cells Using an Atomic Force Microscope,*" Journal of Histochemistry and Cytochemistry, vol. 48, pp. 719-724 (May, 2000); Grubmuller et al., "*Ligand Binding: Molecular Mechanics Calculation of the Streptavidin-Biotin Rupture Force,*" National Library of Medicine Science, 16:271(5251:954-5 (February 1996); Moy et al., "*Intermolecular Forces and Energies Between Ligands and Receptors,*" National Library of Medicine, Science, 266(5183):257-9 (October, 1994); and Moy et al. "*Adhesion Forces Between Individual Ligand-Receptor Pairs,*" National Library of Medicine, Science, 264(5157): 415-7 (April, 1994).

Chemicals or chemical constituents, including atoms and molecules, that are specifically attracted to each other will orient themselves, when in proximity to each other, in a way that maximizes the attraction (or minimizes repulsion), and will seek to eliminate such forces by combining or repelling each other in order to achieve the lowest energy state between attracted or repulsed molecular pairs. There are numerous examples of such attractive and repulsive affinity forces in nature, including formation or dissociation of compounds and explosions or implosions. The forces that result in "affinity" between molecules may be electrostatic, magnetic, nuclear, or a combination thereof, but all share the principle of seeking the lowest possible energy state for a system.

Molecular attractive forces are typically the result of complimentary electric charges exerted by the molecules on each other at chemical binding or epitope sites. Such attraction causes the molecules to orient themselves in a particular way whenever the medium in which the molecules are presents permits such orientation, so as to maximize the attractive forces among complimentary molecular pairs that are seeking to bond with each other.

In this fashion, for example, enzyme-substrate and antigen-antibody pairs "search-out" each other, and such interactive molecular search eventually culminates in molecular attachments of the molecular pairs. The prerequisite for such attachment is the proper spatial molecular orientation of the molecules in the solution. It is envisioned that the interactive molecular pairs that form such attachments must go through certain sequentially distinct steps prior to attachment. The proposed steps are as follows:

1. Molecules are dissolved in a liquid media such as water.
2. They are brought within the proximity of their complimentary molecular pairs by mixing or some other means.
3. The molecules spatially orient themselves to expose their active sites to each other.
4. The molecules then attach to each other, and consequently through attachment and reaction attain a lower energy state.

FIG. 1 is a crude illustration of the manner in which a first molecule MM attaches to a second molecule TM. The present invention is based on the principle that if one could measure either the attractive forces or the orientation of the attracted molecular pairs that are highly specific for each other, one could detect the presence of their "complimentary molecules" even before those molecules combine or react with each other. It is also based on the principle that the greater the concentration of complimentary molecules in proximity to one another, the greater the sum of the attractive force among them, in which case molecular orientation will occur more readily and at greater distances between the complimentary molecules. To date, these principles do not appear to have been exploited as a way to detect the presence and/or concentration of chemicals, molecules, or atoms across a barrier.

SUMMARY OF THE INVENTION

It is accordingly an objective of the invention to provide an apparatus and method for detecting the presence and measuring the concentration of molecules from a distance and/or through a barrier, that is simple to implement, and that does not require radiation or complex computational techniques.

These objectives are accomplished, in accordance with the principles of a preferred embodiment of the invention, by utilizing the principle of chemical/electrostatic attraction (hereinafter "affinity"), i.e., the affinity between charged molecules that cause their chemical interactions and reactions, to infer, based on the behavior of atoms or molecules on one side of the barrier, the presence and concentration of corresponding molecules on the other side of the barrier.

The invention thus provides a method and apparatus that operates by measuring the forces that act on, or at least result in, the molecular orientation of one specific complementary molecule of a molecular affinity pair (the "measuring" molecule), in order to determine the identity and the concentration of the "other" molecule of the pair (the "target" molecule) when the other molecule is in close enough proximity for the forces of attraction to produce a molecular event such as rotation.

It is to be understood that even though the invention is described as being applicable to detection of molecules, the method and apparatus of the invention may also be applied to the detection of other chemical entities, both inorganic and organic, made up of molecules or groups of molecules, and to constituents of molecules such as individual atoms or groups of atoms. Furthermore, although the invention is described as being applicable to detection of molecules through a barrier, the method and apparatus of the invention may also be applied to the detection of molecules over a distance, even though a physical barrier might not be present.

As discussed above, one measurable manifestation of the forces between molecules is the spatial orientation of specific molecules, which may be measured in a variety of ways depending on the properties of the measuring molecules and the material or solution in which the molecules are situated. The claimed invention is not intended to be limited to a particular orientation detection means, but rather is intended to apply to all such means, so long as the orientation detection is used to determine the presence and concentration of a complimentary attracted pair of molecules when the molecules are brought in close enough proximity to each other to exert a force great enough to change the spatial orientation of the molecules.

The following principles may be applied to the spatial orientation "measurement":

1. The speed and magnitude of molecular re-orientation is relatable to the concentration of the complimentary molecules, to the affinity of the complimentary molecules for each other, and to the distance between them.
2. The speed of orientation is an inverse function of the distance between the molecular pairs, and directly relatable to their affinity for each other.
3. If measurement of either the magnitude of such "affinity forces" or the speed and magnitude of molecular pair orientation are measurable in some fashion, then such magnitude and speed should be relatable to the concentration of the molecular pairs even before the molecular pairs attach to each other.
4. Given high enough affinity of molecular pairs, the electrostatic forces may be measurable even if the molecular pairs are brought near one another but are still at significant distances from each other, such as through barriers like membranes and air. It is expected that the nature of the barrier will also exert a significant influence on the magnitude of the affinity, such as on the electrostatic forces between the pairs.

Even though the preferred embodiments of the invention described herein all involve detection of the presence of biochemical analytes in an organism from outside the organism, it will be appreciated that the principles of the invention may also be extended to utilize affinity force affects for purposes other than "detection," i.e., the changes in physical or chemical properties of the measuring agents or molecules may be utilized for some predetermined purpose other than merely detection of the presence of biochemical analytes, such as causing some action or reaction to occur through a barrier and over a distance, transmitting a message, and so forth.

DETAILED DESCRIPTION OF THE PREFERRED EMBODIMENTS

Figure 1:
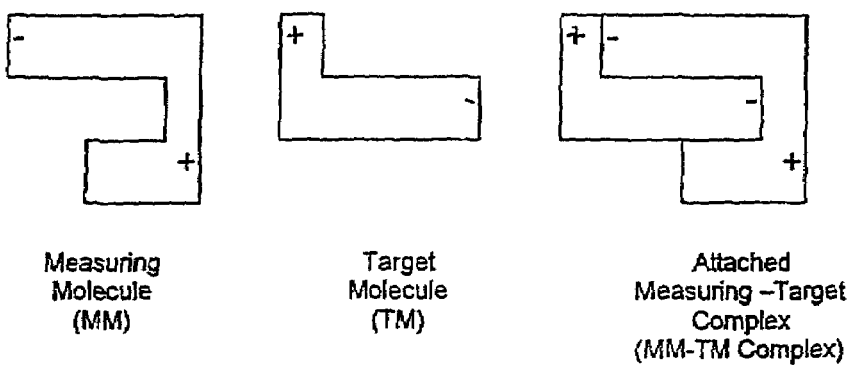
FIG. 1 is a schematic illustration of the principle of molecular affinity used by the preferred embodiments of the invention.
Figure 2:
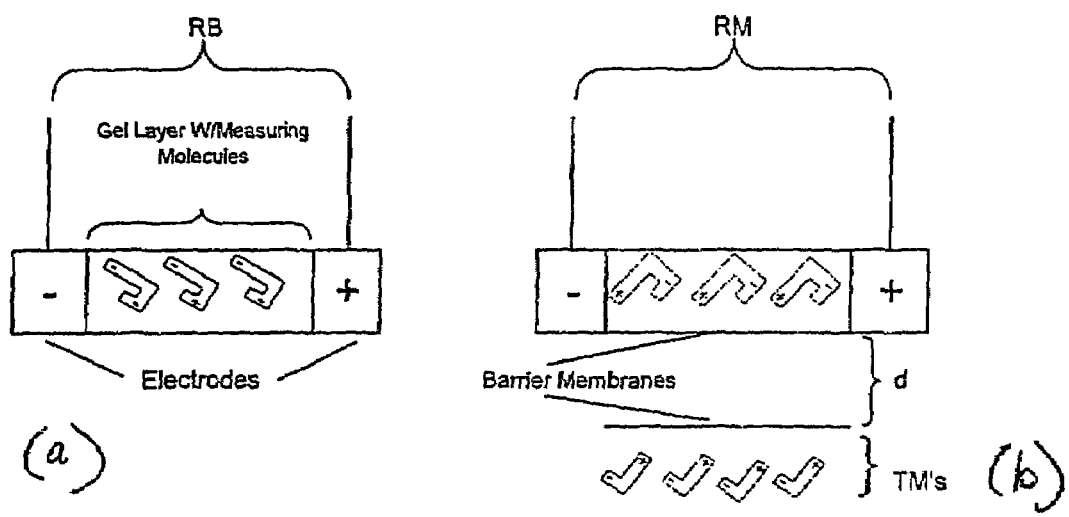
FIG. 2(a) is a schematic diagram of a measuring probe constructed in accordance with the principles of the invention.
FIG. 2(b) shows the measuring probe of FIG. 2(a) after it has been brought into proximity to a barrier membrane and the target molecules on the opposite side of the membrane.

FIG. 2(a) illustrates a gel membrane probe constructed in accordance with the principles of a preferred embodiment of the present invention. The measuring probe includes:

a plurality of measuring molecules having an affinity for the target molecules whose concentration is to be measured;

a solution that permits the measuring molecules to change their orientation when attracted or repelled by the target molecules;

means for measuring the orientation of the measuring molecules.

The type of molecules used as measuring molecules depends on the type of molecules to be measured. For example, if the target molecule is an antibody, then the measuring molecule may be an antigen. Alternatively, to measure concentration of an enzyme, a corresponding "reaction substrate" or "reaction product" may be used. The preferred embodiments of the invention are in principle applicable to any two types of molecules that attract or repel each other on a molecular level by a force sufficient to cause effects at the distance, or across the barrier, separating the measuring and target molecules during a measurement.

An example of an enzyme-substrate pair to which the principles of the invention may be applied is a glucose enzyme-glucose pair such as glucose oxidase-glucose, glucose dehydrogenase-glucose, or glucose mutarotase-glucose. Glucose is usually monitored in diabetics and sometimes referred to as blood sugar. An example of a suitable antibody antigen pair is CRP specific monoclonal antibody—CRP, the detection of which in blood is used to determine the presence and severity of infections present in the body. Alternatively, the target molecule could be an antigen and the measuring molecule could be an antibody.

Other examples of target molecules to which the device of the invention may be applied include immunogobulins such as IgG, IgM, and IgA, and lipoproteins. In addition, the device may be used for non-invasive detection of allergic reactions, difficult to detect diseases or infections caused by microorganisms such as viruses or bacteria, and any other type of infection or immune system reaction to a chemical or biological entity.

The solution in which the measuring molecules are suspended or otherwise situated will depend on the type of measuring molecule. For example, in the illustrated example, the solution is a gel. Alternatively, it might be possible to use liquids, solids, or other materials to contain the measuring molecules while permitting changes in orientation in response to the presence of the target molecule. In addition, the solution in which the measuring molecules are contained may include cofactors as necessary to increase the attractive or repulsive forces.

In the example illustrated in FIGS. 2(a) and 2(b), electrodes are positioned on either side of the solution to enable measurement of the resistivity of the solution to an applied electric current. The change in resistance $\Delta R$ of a given measuring molecule (MM) laden gel layer when brought into proximity with complimentary target molecules (TM) across a barrier, such as a patient's skin, is a function (f) of the affinity (a) or attractive/repulsive force of the MM-TM pair, the concentration of target molecules CTM, and the inverse of the distance (d) between the complimentary molecules. This may be expressed mathematically as follows:

$$\Delta R \propto f\left(\frac{aCTM}{d}\right)$$

where $\Delta R = RB - RM$, RB is the resistivity of the gel layer before being brought into proximity of the target molecules, RM is the resistivity of the gel layer after being brought into proximity with the gel layer, (f) is any function, whether linear or non-linear, that describes the relation between $\Delta R$ and aCTM/d, and both the function (f) and affinity variable (a) depend on the nature of the affinity pair.

In addition to resistivity or conductivity, there are several ways in which the molecular orientation may be measured using this set up, including changes in the nuclear magnetic resonance (NMR) of the molecules, or measurement of changes in other properties of the solution, including electrical, magnetic, or optical properties, that are affected or caused to be affected by molecular orientation. Those skilled in the art will understand that measuring molecules may be modified, for example, by providing chemically labeled cofactors, etc., to enhance the affinity forces on the target molecules.

Furthermore, those skilled in the art will appreciate that spatial orientation may not be the only molecular property affected by the presence of the target molecules. For example, affinity forces may affect the phenomenon of electrophoresis, in which the molecules migrate across the gel in response to an applied field. Those skilled in the art will appreciate that changes in such migration may be used instead of, or in addition to, orientation as a way of detecting the presence of affinity forces between the measuring and target molecules.

Practical Implementation

Practical implementation of the probe illustrated in FIGS. 2(a) and 2(b) requires a probe that can induce uniform molecular rotation in a sample of measuring molecules, to provide a baseline against which target molecule induced changes can be detected. For many applications, at least a 98% rotation will be required. This unidirectional rotation of measuring molecules may be verified by conventional fluorescence optical spectroscopy techniques.

In a preferred embodiment of the invention, in order to achieve the required unidirectional rotation, a uniform unidirectional current may be applied to a measuring molecule solution that has been uniformly applied on the measuring film, or that is homogeneously situated in a gel-like media. The uniform current and verification of the current is provided by an electrophoretic device capable of unidirectional current induction and planar conductivity measurement in a 360° array, currently envisioned to be a perpendicular mode relative to the applied current. A roller-type temperature controlled gel coating device may be used to achieve uniform application of the measuring molecular solution, preferably to a uniform thickness of between a few angstroms (to accommodate at least one layer of measuring molecules and allow for their unhindered molecular rotation) to a few millimeters. The gel-like media may, by way of illustration and not limitation, be a non-polar gel media readily soluble in water capable of producing a homogenous solution of measuring molecules, and that is liquid between 40-60° C. and that forms a gel-like solid between 5-40° C.

Upon achieving uniform rotation of the measuring molecules, implementation of the invention requires monitoring of molecular orientation, preferably to a rotation accuracy of at least +5%, which may again be verified by fluorescence spectroscopy of fluorescent labeled measuring molecules.

Once it is possible to "see" the spatial configuration of the uniformly rotated molecules, commercially available measuring devices can be used to measure current variance, directional variance of the applied current, and voltage variance, given a uniformly positioned gel coated film. The conductance of the film at different angles relative to the applied electrophoretic current in the "off" mode, i.e., in the absence of electrophoretic field potential, must then be determined. Commercially available measuring devices are currently capable of measuring resistance along and perpendicular to the current direction in a three dimensional mode, at 10°±2° intervals in a planar 360° array. The key is to be able to measure a small enough change in resistance due to current impedance caused by molecular rotation in the path of the current applied.

The gel media should be selected to have a large variation in directional conductivity between electrophoretic conduction and conduction perpendicular to the electrophoretic field, with minimal time required for complete rotation of the measuring molecules at a constant voltage and current. Widely used gel media include polyacrylamide gel and agarose gels. For each candidate gel, specific electrophoretic parameters of the measuring molecules in each gel should be measured, for a particular apparatus, as a function of concentration, temperature, and solvent composition.

In order for the sensor of the invention to detect rotation of the measuring molecules in response the presence of target molecules, as described above, it is helpful to determine the exact effect of measuring molecule rotation on the conductivity or resistivity of the gel solution. This may be accomplished by measuring conductivity using electrophoretic electrodes when the residual electrophoretic current and voltage is zero, and measuring in a perpendicular plane at ten degree increments to the applied electrophoretic current. The sensor thereby determines the relation between measurable changes in conductivity or resistivity as a function of (a) direction of measuring current relative to the electrophoretic current applied to the gel media, (b) concentration of measuring molecules dissolved in the gel, and (c) electrophoretic field application time necessary for complete uniform rotation of the measuring molecules. The rotation of the measuring molecules may be monitored and verified by a fluorescence optical rotation measuring device.

Once a correlation between applied current and measuring molecule rotation is established, the effect of target solution concentration and proximity of target molecules on the conductance or resistivity of the gel solution can be established by measuring the conductance or resistivity of the gel solution for different target solutions. If a measurable difference in rotation of the measuring molecules is detected, a relationship between target distance and measuring molecule rotation can be established for different molecular pairs. Rotation of the measuring molecules in response to proximity of target molecules can again be verified by fluorescence optical spectroscopy.

Probe Prototype

Figure 3:
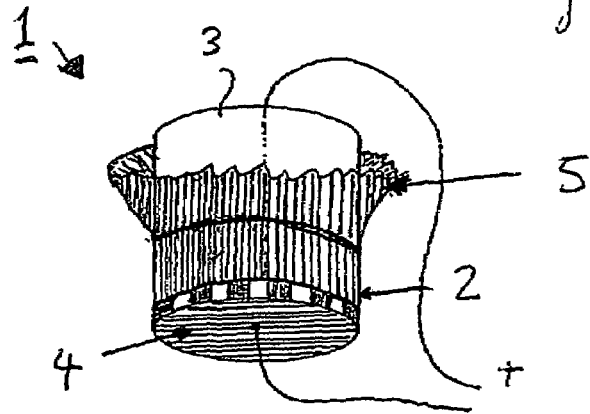
FIG. 3 is an illustration of a probe prototype.

A probe prototype 1 that can be used to verify directional conductance or resistivity changes in response to rotation of measuring molecules, to establish the composition and thickness of the gel media, and to identify the choice and concentration of measuring molecules necessary for targeted sensitivity, is illustrated in FIG. 3. The probe prototype is a modified electrophoretic cell including a cylindrical body 2 having respective electrodes 3 and 4 at the top and bottom for creating an electrophoretic field across a gel coated membrane 5 wrapped around the cylinder. The electrophoretic field causes the measuring molecules in the gel to orient relative to the field, at which time current to the electrodes is switched off or the effect of the electrodes is neutralized or removed, and the resistance for the gel coated film is measured perpendicular to and across the 360° array. As indicated above, once a suitable gel is found and a correlation between rotation of the measuring molecules and the resistance of the gel coated film is established, then measurements can also be made in the presence of target molecules, for example, by bringing the coated membrane into contact with a beaker of solution of the target molecules.

For the next phase of verification, the probe should be sensitive enough to produce a measurable change in resistivity when ±5% of the measurement molecules rotate, precise enough to achieve a ±10% coefficient of variation for a standard solution of target molecules at an upper limit of a clinical normal range of the target, and sufficiently accurate to reproduce standard curves of pure target solution with equimolar mixtures of nonspecific homologues to within ±15% coefficient of variation. Ultimately, a practical version of the probe with require a sensitivity of at least ±2%, precision of ±5%, and accuracy, using actual patient serum/blood sample with the following minimum correlation parameter values versus a standard reference method, of 0.9±0.1 regression coefficient, 0.9±0.15 slope, and Y intercept of ±10% of the lower limit of a clinical normal range.

Having thus described a preferred embodiment of the invention in sufficient detail to enable those skilled in the art to make and use the invention, it will nevertheless be appreciated that numerous variations and modifications of the illustrated embodiment may be made without departing from the spirit of the invention, and it is intended that the invention not be limited by the above description or accompanying drawings, but that it be defined solely in accordance with the appended claims.

What is claimed is:

1. A method for detecting, through a barrier, whether target entities are present in a sample suspected of containing said target entities, comprising the steps of:

providing a probe in which are situated a plurality of measuring agents;

bringing the probe toward the sample and measuring changes in a characteristic of the measuring agents if said target entities are present in the sample, said changes resulting from affinity forces between the target entities and the measuring agents, the affinity forces causing said changes to occur even though said target entities and measuring agents are separated by said barrier; and inferring that said target entities are present in said sample if said changes are measured, and inferring that said target entities are not present in said sample if said changes are not measured, wherein said target entities are glucose molecules.

2. A method as claimed in claim 1, wherein said measuring agents include a measuring molecule.

3. A method as claimed in claim 2, further comprising the step of determining, based on said measurement of changes, a concentration of said target molecule.

4. A method as claimed in claim 2, wherein the characteristic is spatial orientation.

5. A method as claimed in claim 4, wherein said measurable changes are measurable changes in said orientation that are detected by measuring a resistivity of a material in which said measuring molecule is suspended.

6. A method as claimed in claim 5, wherein said material, in which said measuring molecule is suspended, is a gel.

7. A method as claimed in claim 4, wherein said target entities include a substrate and said measuring molecule is an enzyme.

8. A method as claimed in claim 4, wherein said measuring molecule is a glucose enzyme.

9. A method as claimed in claim 8, wherein said measuring molecule is glucose oxidase, glucose dehydrogenase, or glucose mutarotase.

* * * * *